US007003069B2

(12) United States Patent
Tsujii

(10) Patent No.: US 7,003,069 B2
(45) Date of Patent: Feb. 21, 2006

(54) RADIOGRAPHIC APPARATUS, RADIOGRAPHIC METHOD, PROGRAM, AND COMPUTER-READABLE STORAGE MEDIUM

(75) Inventor: Osamu Tsujii, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/008,050

(22) Filed: Dec. 8, 2004

(65) Prior Publication Data

US 2005/0129180 A1    Jun. 16, 2005

(30) Foreign Application Priority Data

Dec. 16, 2003    (JP)    ............................. 2003-417976

(51) Int. Cl.
 *A61B 6/00*    (2006.01)
(52) U.S. Cl. ............................................ 378/8; 378/62
(58) Field of Classification Search .................. 378/4, 378/8, 20, 62, 95, 117, 195
See application file for complete search history.

(56) References Cited

U.S. PATENT DOCUMENTS

| 5,811,790 A | 9/1998 | Endo | 250/208.1 |
| 5,965,872 A | 10/1999 | Endo | 250/208.1 |
| 6,049,074 A | 4/2000 | Endo | 250/208.1 |

FOREIGN PATENT DOCUMENTS

| JP | 06-304164 A | 11/1994 |
| JP | 07-124151 A | 5/1995 |

*Primary Examiner*—Edward J. Glick
*Assistant Examiner*—Courtney Thomas
(74) *Attorney, Agent, or Firm*—Canon, U.S.A. Inc. I.P. Div

(57) ABSTRACT

A radiographic apparatus includes an X-ray generator for irradiating a subject with X-rays, a rotating unit for rotating the subject irradiated with the X-rays, a two-dimensional detector for converting X-rays transmitted through the subject into projection-image data, an information extracting unit for extracting information regarding the subject from the projection-image data, a calculating unit for calculating an amount of shift, with respect to a vertical direction, of at least one of the X-ray generator, the two-dimensional detector, and the subject, based on the information extracted, a driving unit for changing a position, with respect to the vertical direction, of at least one of the X-ray generator, the two-dimensional detector, and the subject, and a controlling unit for controlling the driving unit according to the amount of shift calculated by the calculating unit.

10 Claims, 5 Drawing Sheets

RADIOGRAPHIC APPARATUS, RADIOGRAPHIC METHOD, PROGRAM, AND COMPUTER-READABLE STORAGE MEDIUM

BACKGROUND OF THE INVENTION

1. Field of the Invention

The present invention relates to radiographic apparatuses for capturing two-dimensional projection image data using a cone-beam X-ray from an X-ray generator and reconstructing three-dimensional image data. Particularly, the present invention relates to a radiographic apparatus that allows a position of a subject relative to an X-ray generator and a sensor to be adjusted based on information obtained from two-dimensional projection-image data.

2. Description of the Related Art

Recently, in order to obtain digital data for a large screen, two-dimensional detectors (also referred to as flat panel detectors (FPDs)) for X-ray imaging are being developed, as disclosed, for example, in Japanese Patent Laid-Open No. 09-288184, corresponding U.S. Pat. Nos. 5,811,790, 5,965,872, and 6,049,074. Particularly, for simple imaging, X-ray imaging apparatuses including two-dimensional detectors with large photoreceptor surfaces having a size of 43 cm×43 cm are coming into practical use. X-ray imaging devices including two-dimensional detectors having large photoreceptor surfaces are referred to as cone-beam computed-tomography (CT) apparatuses (hereinafter referred to as "CBCT apparatuses").

When imaging is carried out with a CBCT apparatus, an X-ray technologist assumes an approximate position of a target organ of a subject.

Also, helical CT apparatuses are known. In a helical CT apparatus, a subject is irradiated with X-rays. X-rays that transmit through the subject are detected by an X-ray detector, and transparent image data of the subject (referred to as a scanogram or SCOUT image data), a tomogram, or three-dimensional image data is obtained based on the X-ray detection output (the number of photons in the X-rays).

In the helical CT apparatus, in order to determine a scanning region, i.e., a region of a subject to be scanned, scanogram image data or SCOUT image data is obtained. According to techniques disclosed in Japanese Patent Laid-Open No. 07-124151, when the entire lung regions are to be imaged, since the positions of the entire lung regions cannot be identified from the appearance, a range of the entire lung regions is determined based on the scanogram, image data, and a range to be imaged by the CT apparatus is determined while scanning the subject. More specifically, according to the method disclosed, a profile of the pattern of scanogram image data with respect to the direction across the body is analyzed to identify the lung regions.

According to techniques disclosed in Japanese Patent Laid-Open No. 06-304164, laser beams are emitted, a region shielded by a subject is detected by an optical sensor to estimate a chest region of the subject, and the region is helical-scanned.

In a CBCT apparatus, X-rays reach a sensor while spreading in the direction of body axis (the direction of Z axis), so that the resolution of reconstructed image data in the periphery of the sensor with respect to the direction of body axis is lower compared with that in a central region of the sensor. Thus, an imaging system must be positioned so that a region of particular interest in the subject is located in the proximity of the central region of the sensor. However, when the position of a target organ of a subject to be imaged is assumed approximately, it is difficult to locate the target organ suitably in an imaging range of a sensor. Hereinafter, a point where a center of a flux of X-rays emitted from an X-ray generator reaches will be referred to as a radiation center. The radiation center is a point where a center of a flux of X-rays reaches, at which the resolution of image data is usually highest. This is because X-rays perpendicularly cross the sensor surface at the radiation center. Generally, imaging is carried out so that the radiation center matches the center of the sensor.

As for a helical CT apparatus, the cone angle is small, so that a subject is imaged with a plurality of revolutions. That is, a focus of an X-ray generator need not be defined in the subject, and scanogram image data is used to determine a range for imaging a subject by a plurality of revolutions. Thus, according to the method that uses scanogram image data, although it is possible to determine a range for imaging a subject, it is not suggested to set a radiation center, so that it is not possible to determine a radiation center.

Similarly, according to the method that uses laser beams, although it is possible to determine a range for imaging a subject, it is not possible to determine a radiation center.

SUMMARY OF THE INVENTION

The present invention is directed to a radiographic apparatus, a radiographic method, a program, and a computer-readable storage medium that allow a position of a subject relative to an X-ray generator and a two-dimensional detector to be changed by extracting information regarding a region of an anatomical organ from projection-image data.

In one aspect of the present invention, a radiographic apparatus is provided. The radiographic apparatus includes an X-ray generator operable to irradiate X-rays at a subject; a rotating unit operable to rotate the subject irradiated with the X-rays; a two-dimensional detector converting the X-rays transmitting through the subject to obtain projection-image data; an information extracting unit extracting information including information regarding the subject from the projection-image data; a calculating unit calculating an amount of shift, with respect to a vertical direction, of at least one of the X-ray generator, the two-dimensional detector, and the subject, based on the information extracted by the information extracting unit; a driving unit changing a position, with respect to the vertical direction, of at least one of the X-ray generator, the two-dimensional detector, and the subject; and a controlling unit controlling the driving unit according to the amount of shift calculated by the calculating unit.

According to another aspect of the present invention, a radiographic method of radiographing a subject with a radiographic apparatus including an X-ray generator, a rotating unit, and a two-dimensional detector includes: irradiating the subject with X-rays from the X-ray generator to obtain projection-image data; extracting information regarding the subject from the projection-image data; calculating an amount of shift, with respect to a vertical direction, of at least one of the X-ray generator, the two-dimensional detector, and the subject, based on the information extracted in the information extracting step; and changing a position, with respect to the vertical direction, of at least one of the X-ray generator, the two-dimensional detector, and the subject, according to the amount of shift calculated in the calculating step.

According to another aspect of the present invention, a program stored on a recording medium and executable by a computer to perform the radiographic method disclosed above.

According to another aspect of the present invention, a computer-readable storage medium having recorded thereon the program disclosed above.

Further features and advantages of the present invention will become apparent from the following description of the embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

Embodiments of the present invention will now be described in accordance with the accompanying drawings.

Figure 1:
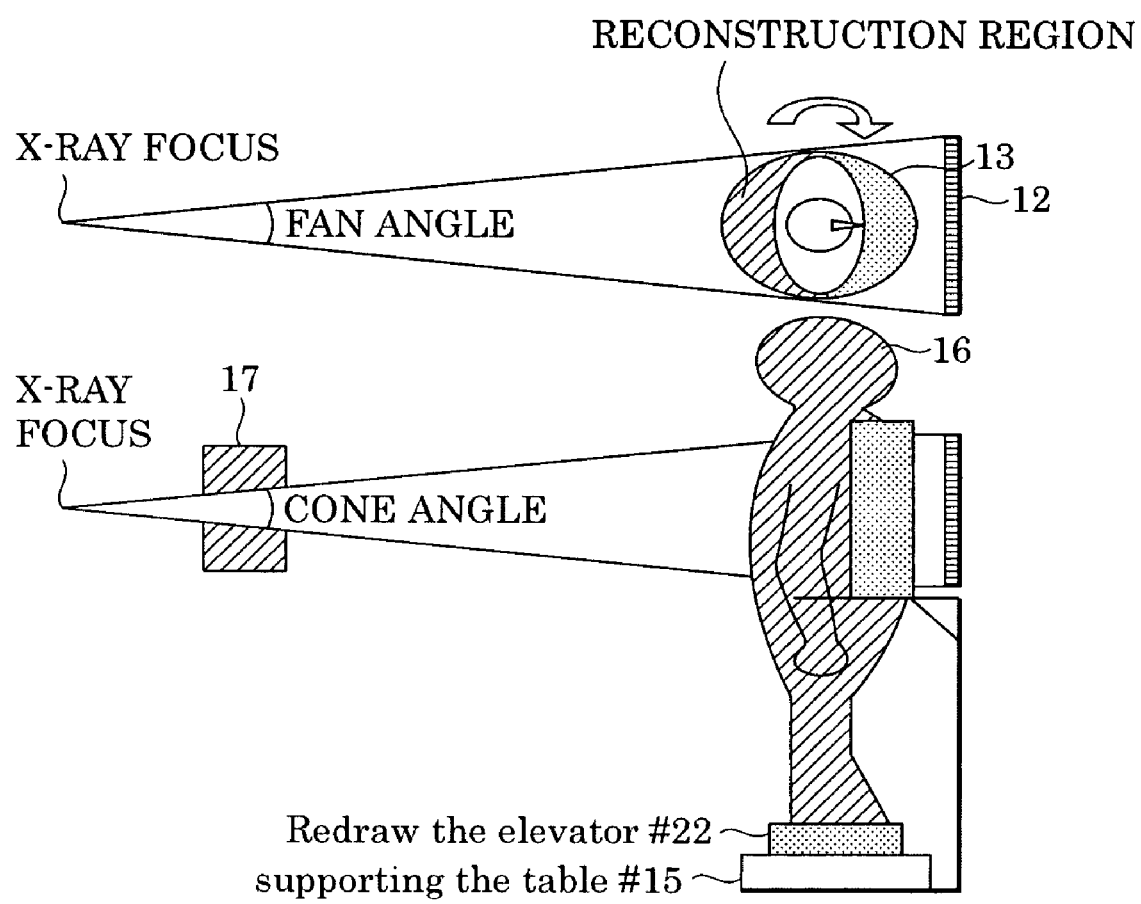
FIG. 1 is an illustration of a geometric system for imaging.

FIG. 1 shows a top view and a side view showing an example construction of a CBCT apparatus of a type in which a subject can be rotated. Referring to FIG. 1, an X-ray generator 11 (shown in FIG. 2) emits cone-beam X-rays from an X-ray focus. As shown in FIG. 1, the angle of X-ray spreading with respect to a vertical direction is referred to as a cone angle, and the angle of X-ray spreading with respect to a horizontal direction is referred to as a fan angle. A rotation table 15 serves to rotate a subject 16 mounted thereon and irradiated with X-rays emitted from the X-ray generator 11. A chest pad 13 is used to fix the position of the subject 16, and is supported by a pole fixed on rotation table 15.

A two-dimensional detector 12 converts X-rays into electric signals. X-rays that are emitted from the X-ray generator 11 and that transmit through the chest pad 13, the subject 16, and a scatter-filtering grid (not shown) are received by the two-dimensional detector 12. The two-dimensional detector 12 converts the received X-rays into electric signals to obtain projection-image data. X-rays are repeatedly emitted and received while the rotation table 15 is rotating, thereby collecting projection data as captured from multiple directions. Since rotation is relative, alternatively, the X-ray generator 11 and the two-dimensional detector 12 may be rotated with the subject 16 fixed. A table elevator 22 is disposed under the rotation table 15, and it allows adjusting the height of the rotation table 15. The relationship between a region of the subject 16 to be imaged and the height of the two-dimensional detector 12 can be adjusted by moving the subject 16 upward or downward by the table elevator 22. Although the subject 16 is moved upward or downward by the table elevator 22 in this embodiment, alternatively, the relationship between a region of the subject 16 to be imaged and the height of the two-dimensional detector 12 can be adjusted by moving the two-dimensional detector 12 upward or downward. In that case, a driving motor (not shown) for moving the two-dimensional detector 12 upward or downward with the pole as a rail is provided on a back surface of the two-dimensional detector 12.

As an example construction of the two-dimensional detector 12, the size of each pixel is 250×250 $\mu$m, and the size of the sensor is 43×43 cm. In this case, the number of pixels is 1,720×1,720.

Similarly, the X-ray generator 11 can be moved upward or downward by a driving unit (not shown). The driving unit works in cooperation with the driving motor so that the X-ray generator 11 and the two-dimensional detector 12 are moved by the same distance when either of the driving unit and the driving motor is driven.

The range of an actual space for which three-apparatus dimensional data is to be reconstructed by the CBCT is referred to as a reconstruction region, which is usually cylindrical in shape. The height of the reconstruction region is referred to as a height of view, which is hereinafter abbreviated as HOV. The radius of the reconstruction region is referred to as a field of view, which is hereinafter abbreviated as FOV. The angle of X-ray spreading with respect to the direction of a body axis (the direction of a Z axis, or a vertical direction) is referred to as a cone angle, and the angle of X-ray spreading with respect to a horizontal direction is referred to as a fan angle.

Figure 2:
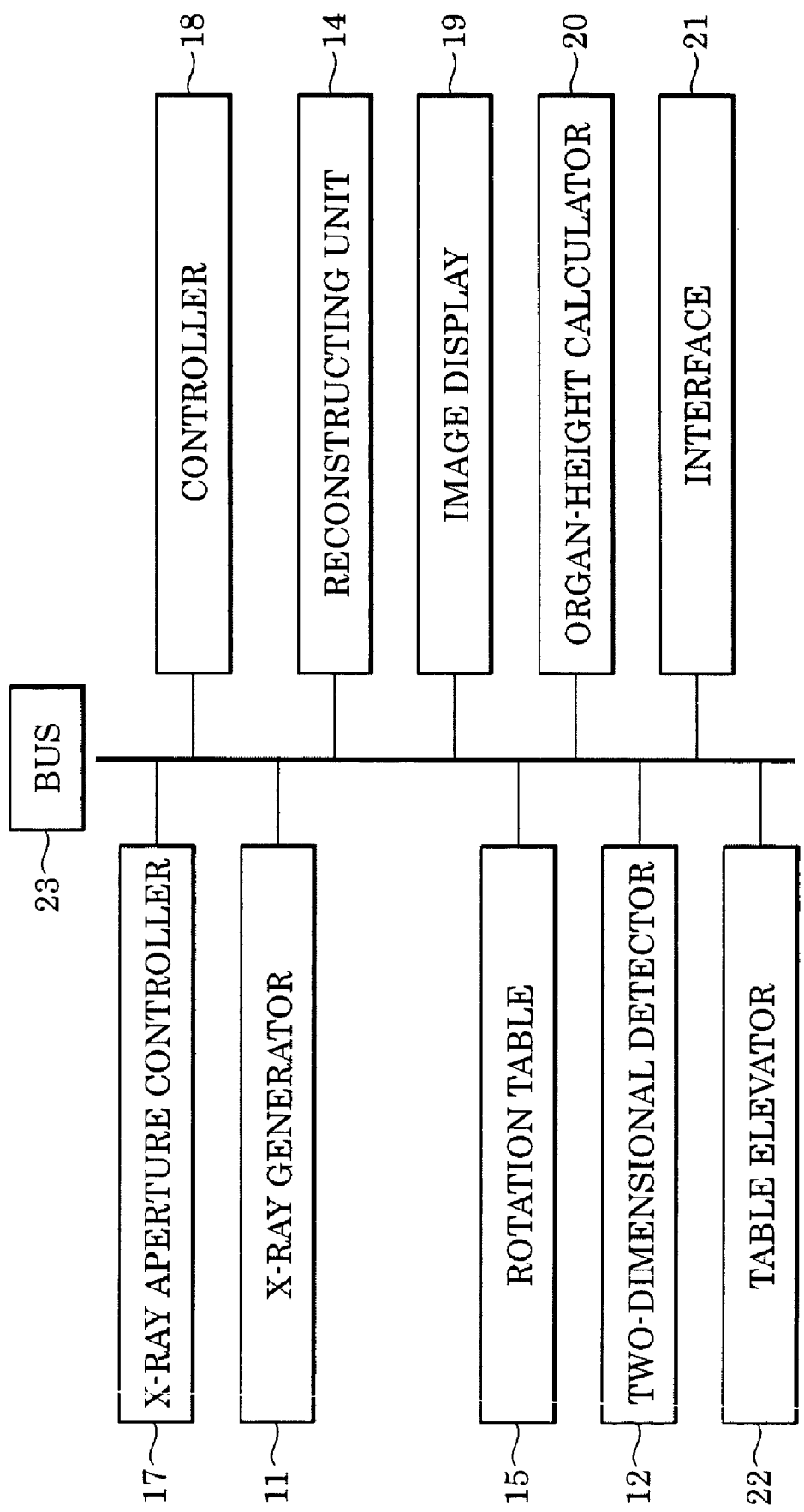
FIG. 2 is a block diagram of a system according to an embodiment of the present invention.
Figure 6:
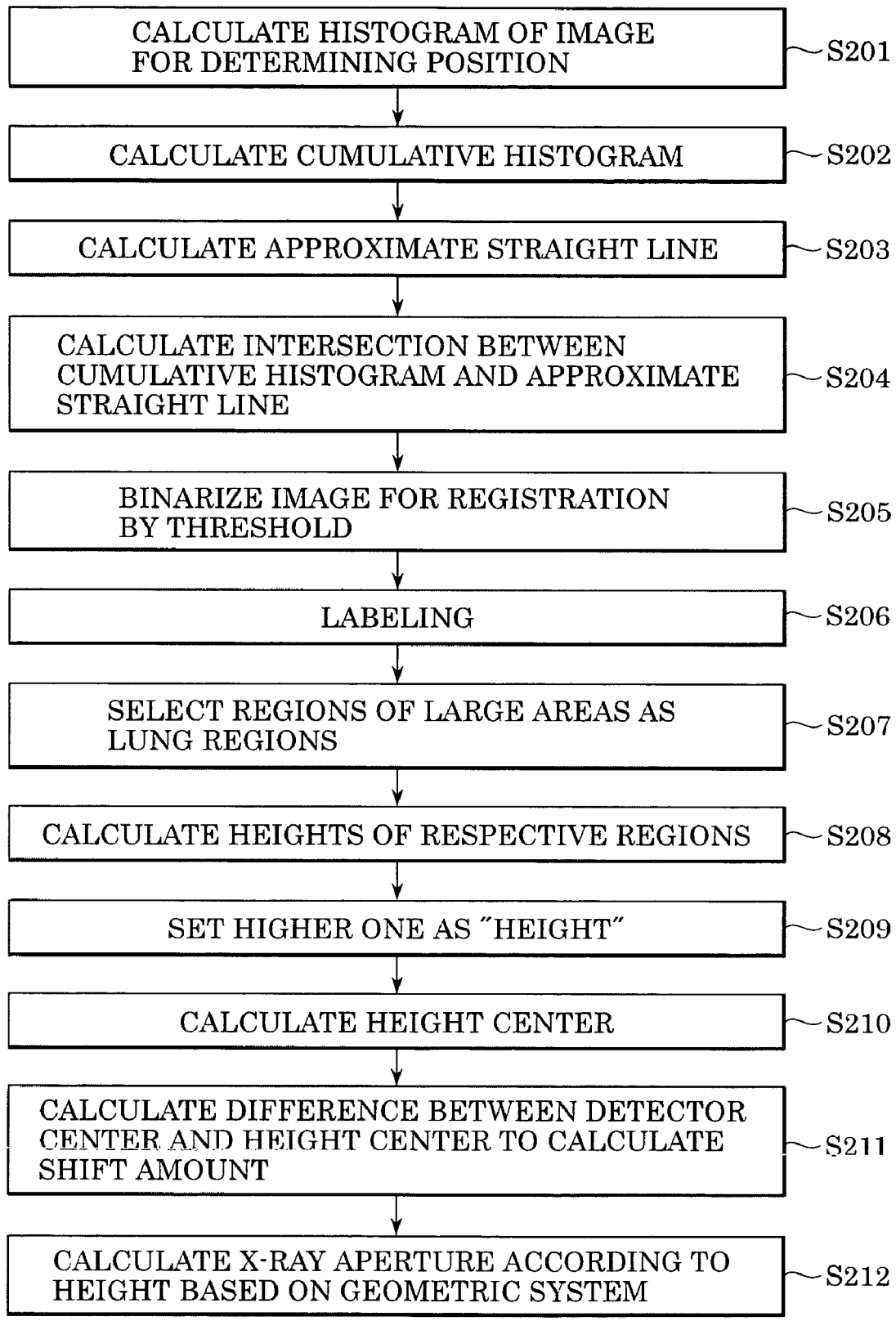
FIG. 6 is a flowchart of a procedure for calculating a height of lung regions, an amount of shift in height, and an amount of change in X-ray aperture.

FIG. 2 is a diagram showing an example system construction according to an embodiment of the present invention. Referring to FIG. 2, a bus 23 allows exchanging control signals and data. A controller 18 corresponds to a central processing unit (CPU) of a computer, and it controls the entire system together with a main memory (not shown). The main memory stores various data or other information needed for processing by the controller 18, and it includes a work memory for the controller 18. Program code according to flowcharts shown in FIGS. 3 and 6 are stored in the main memory or a read-only memory (ROM) that is not shown, and is read and executed by the controller 18.

A reconstructing unit 14 is special hardware that applies pre-processing, filtering, and back projection on two-dimensional image data to reconstruct three-dimensional CT image data from plural sets of projection-image data. An image display 19 displays reconstructed CT image data. An organ-height calculator 20 calculates the height of lung regions or a chest with respect to the direction of a body axis. An interface 21 is used to present a message to a user or to select input information. The X-ray generator 11 generates continuous X-rays. An X-ray aperture controller 17 shapes the form of X-ray beams emitted from the X-ray generator 11.

Figure 3:
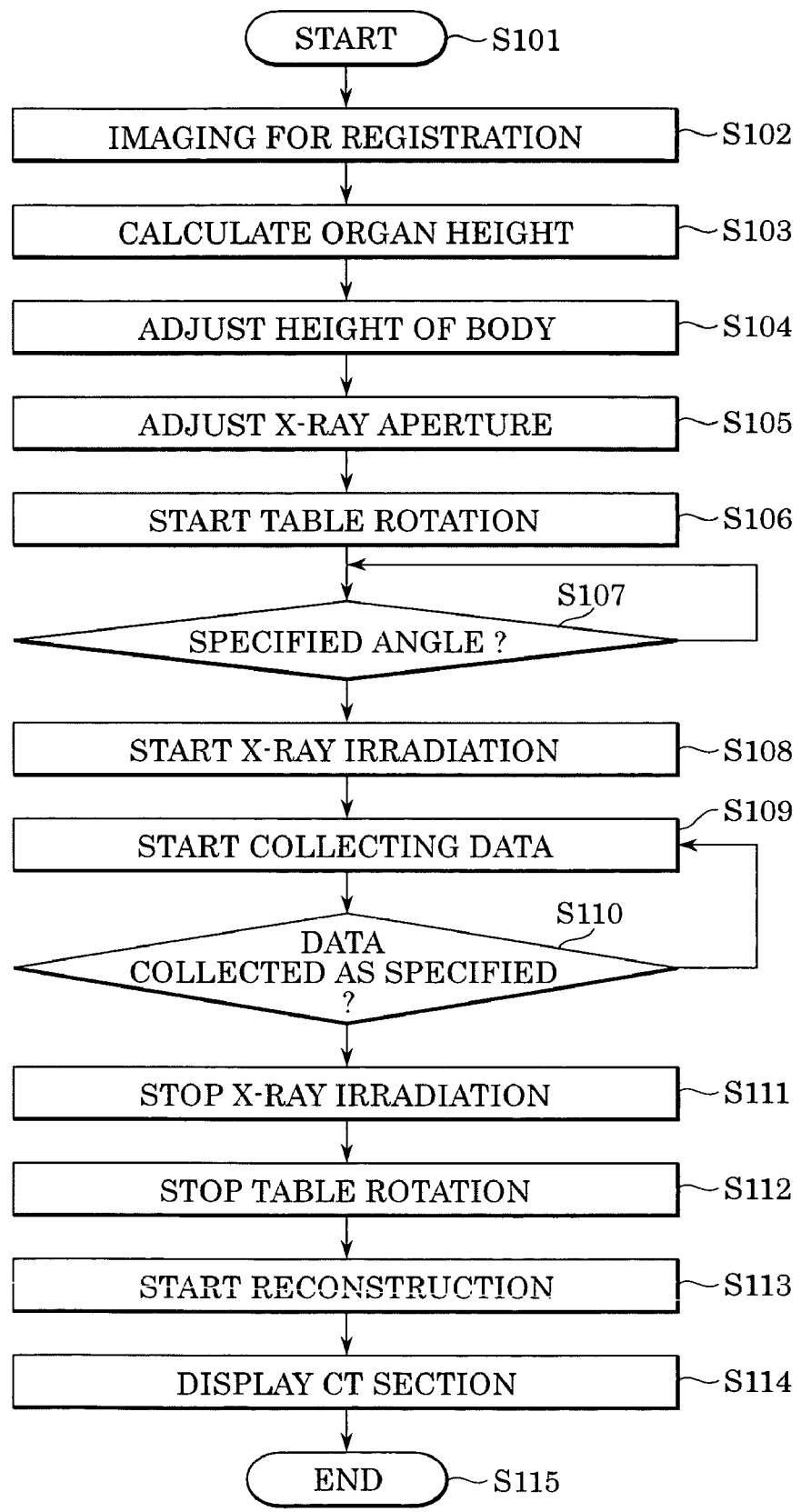
FIG. 3 is a flowchart according to the embodiment.

FIG. 3 is a flowchart of an imaging process executed by the CBCT apparatus. With reference to the flowchart, an operation of the CBCT apparatus of a type in which a subject can be rotated will be described in the context of an example where a chest is imaged.

First, an instruction for starting imaging is issued via the interface 21 (S101). Then, according to an instruction from the controller 18, an X-ray generating signal is sent to the X-ray generator 11 to carry out X-ray irradiation with a small amount of X-rays to obtain projection-image data for registration (S102). Transmitted X-rays are captured by the two-dimensional detector 12, and resulting signals are transferred to the organ-height calculator 20. The organ-height calculator 20 determines the height of an organ (S103). The organ is herein assumed to be lung regions or a chest.

Although this embodiment is described assuming that the target organ is lung regions or a chest, the target organ may be other organs.

Based on the height of the organ and the position of the organ as detected by the two-dimensional detector 12, the controller 18 drives the table elevator 22 to adjust the height of the subject 16 (S104). At the same time, the controller 18, based on the height of the organ, drives the X-ray aperture controller 17 to control the aperture of X rays in accordance with the height of the organ (S105). The relative height of the subject 16 and the two-dimensional detector 12 can also be adjusted by the driving motor and the driving unit. The relative height of the subject 16 and the two-dimensional detector 12 can be adjusted by moving the subject 16 upward or downward or by moving the two-dimensional detector 12 upward or downward.

After or in parallel with the adjustment of the height of the subject 16 and the adjustment of the X-ray aperture, under the control of the controller 18, the rotation table 15 with the subject 16 fixed thereon starts rotating (S106). The controller 18 monitors encoder signals (not shown) generated by the rotation table 15 to determine whether the rotation has reached a predetermined constant speed and angle (S107). When the rotation reaches the predetermined constant speed and angle, the controller 18 sends a signal to the X-ray generator 11 to start X-ray irradiation (S108). The encoder signals are also used to determine timing of integration. When an encoder that generates 25,000 pulses per one revolution is used, in order to collect 1,000 views per one revolution, data is collected from the two-dimensional detector 12 every 25 pulses of the encoder signals. The controller 18 counts the encoding pulses and generates an integration signal every 25 pulses to count the amount of X-rays that reach the two-dimensional detector 12 (S109).

Although it is assumed in this embodiment that X-rays are generated continuously, without limitation to the embodiment, pulsed X-rays may be generated in accordance with integration segments of the two-dimensional detector 12 based on the encoder signals. The data from the two-dimensional detector 12 is transferred sequentially to the reconstructing unit 14 via the bus 23. The transfer of data is continued until the rotation table 15 is rotated by a predetermined angle so that a predetermined number of views is collected (S110). Then, the controller 18 instructs the X-ray generator 11 to stop X-ray irradiation (S111). Then, the controller 18 controls the rotation table 15 to reduce rotation speed until the rotation table 15 is stopped (S112).

Immediately after the X-ray irradiation is completed, the last projection data is transferred to the reconstructing unit 14. The controller 18 instructs the reconstructing unit 14 to carry out reconstruction based on the collected projection data. The reconstruction is also possible by instructing reconstruction after all the data is collected (S113). The reconstructing unit 14 applies image processing on the projection-image data, such as pre-processing and filtering, and reversely projects the resulting projection-image data, thereby calculating reconstructed image data. The pre-processing includes offset processing, log conversion, and water correction. In this embodiment, the filtering is implemented by the Ramachandran function or the Shepp-Logan function, which is usually the case. Data obtained by the filtering is reversely projected. The algorithm used for filtering and reverse projection in this embodiment is the Feldkamp algorithm. When the reverse projection is completed and CT section image data is reconstructed, the section image data is displayed on the image display 19 (S114). When the section image data is displayed, imaging is finished (S115).

Although the Feldkamp algorithm is used in this embodiment, other reconstruction algorithms may be used. For reference, see Feldkamp, Davis, and Kress, "Practical Cone-Beam Algorithm", J. Opt. Soc. Am. A1, pp. 612 to 619, 1984. The subject 16 stands on the rotation table 15 so that the subject 16 is rotated together.

Figure 4A:
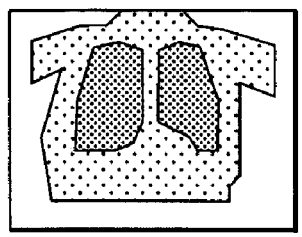
FIGS. 4A and 4B are diagrams for explaining a method of extracting lung regions.
Figure 4B:
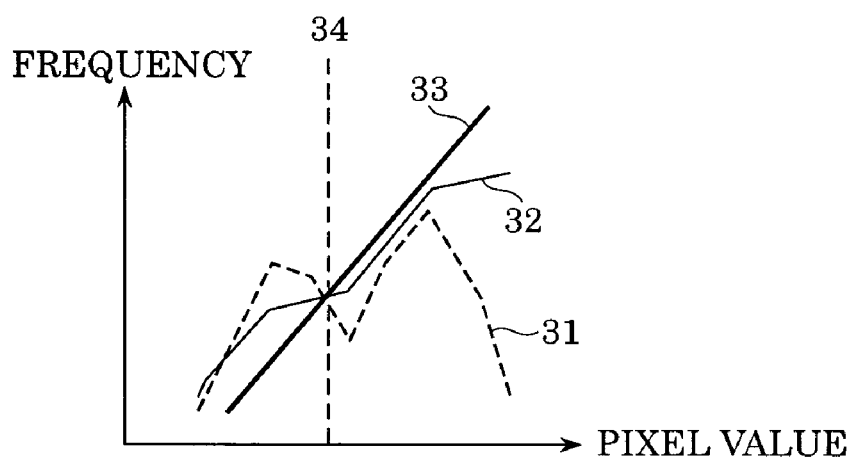
Figure 5:
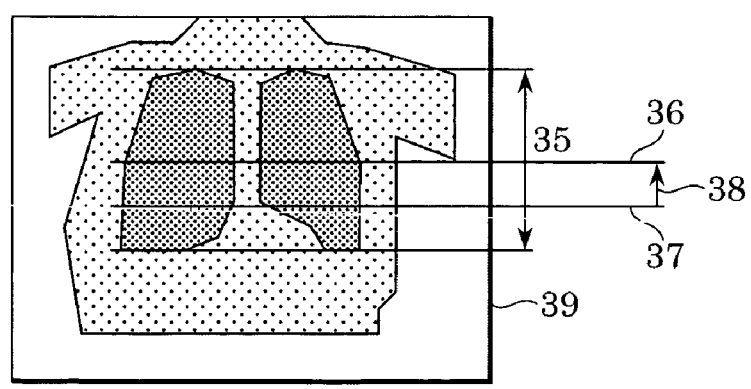
FIG. 5 is a diagram for explaining a method of calculating an amount of shift in height.

Next, the method of calculating the height of an organ (S103), the amount of shift in height (S104), and the amount of change in the X-ray aperture (S105) by the organ-height calculator 20 will be described with reference to FIGS. 4A and 4B. FIG. 4A shows image data of lung regions. FIG. 4B shows a cumulative histogram with a horizontal axis representing pixel value and a vertical axis representing frequency of occurrence, and an approximate straight line is shown. FIG. 5 is a diagram for explaining an amount of shift, and two lung regions on left and right are lung regions extracted by binarization that will be described later.

First, a histogram 31 of chest front image data (e.g., the image data shown in FIG. 4A) that is projection image data obtained for registration is calculated (S201). The histogram is usually bimodal, as indicated by a broken line in FIG. 4B. The mode on the side of larger pixel value corresponds to lung regions. Then, a cumulative histogram 32 of the histogram 31 is calculated (S202), and an approximate straight line 33 of the cumulative histogram 32 is calculated (S203). The intersection between the cumulative histogram 32 and the approximate straight line 33 exists in the proximity of a valley between the two modes. Thus, the intersection is used as a threshold 34 for binarization (S204).

Based on the threshold calculated in step S204, the chest front image data is binarized (S205) to extract approximate lung regions. At this time, however, unneeded regions of small areas exist in the image data, so that labeling is carried out to remove the unneeded regions (S206). Of the labeled regions, two regions of large sizes are selected as left and right lung regions (S207). The other regions are determined as unneeded regions and removed from the binarized image data. Thus, the unneeded regions need not be considered. Then, the coordinate position of the lung regions with respect to the vertical direction is calculated. More specifically, the binarized image data is scanned from the upper side and the position of a pixel detected first is determined as an upper end of the lung regions, and similarly, the image data is scanned from the lower side and the position of a pixel detected first is determined as a lower end of the lung regions (S208 and S209). The distance between the upper and lower ends of the lung regions is determined as a height T 35 of the lung regions. Then, a center Tc 36 of the height T of the lung regions is calculated (S210). Then, the difference between the center Tc 36 of the height T of the lung regions and a center Sc 37 of the two-dimensional detector 12 is calculated to determine an amount M 38 of shift in height (S211). The center Sc 37 of the two-dimensional detector 12 refers to a center with respect to a vertical direction of an outer shape 39 of the two-dimensional detector 12.

Then, according to the value of the height T 35, an amount of aperture is calculated based on the geometric system for imaging shown in FIG. 1 (S212). In this case, the amount of aperture is determined so that the range of the height T 35 is irradiated with X-rays. Similarly, the amount of aperture with respect to the left-right direction (i.e., the horizontal direction) is calculated based on left and right ends of the lung regions. This is possible by using trigonometric functions, as will be readily understood.

In this embodiment, a radiation center of X rays emitted by the X-ray generator 11 is set at a point at the middle of the upper and lower ends of the lung regions and at the middle of the left and right ends of the lung regions. The radiation center refers to a point that the center of a flux of X-rays reaches, at which usually the resolution of image data is highest. By matching the radiation center with an internal point of the extracted region of the anatomical organ (the lung regions in this embodiment), the entire anatomical organ can be imaged efficiently. That is, it is statistically expected that the resolution of the entire anatomical organ is high. The internal point refers to a point calculated based on the region of the anatomical organ extracted. By matching the internal point with the radiation center, the resolution of the observed region improves. Although the internal point is set at the middle of the upper and lower ends and at the middle of the left and right ends of the target anatomical organ, without limitation to the embodiment, the internal point may be set at a point calculated based on information of an anatomical organ. Alternatively, similar advantage can be expected by setting a radiation center at a center of gravity of an anatomical organ extracted in the image data.

With the CBCT apparatus according to this embodiment, an amount of difference for matching the center of the height of an organ and the center of the two-dimensional detector 12 with respect to the direction of a body axis can be calculated. Thus, it is possible to set a position of the imaging system in the CBCT apparatus with respect to a height direction. Thus, CT images of lung regions or a chest of a subject can be captured stably. Furthermore, by matching the center of the height of an organ and the center of the two-dimensional detector 12 with respect to the direction of a body axis, the entire organ can be imaged more stably. Furthermore, CT image data in which a target region for diagnosis is reconstructed in good quality can be obtained. Furthermore, since the imaging system can be positioned at an optimal position, extra imaging region need not be maintained, so that the size of an FPD can be optimally reduced. Accordingly, the cost of a product can be reduced. Furthermore, by controlling the aperture of radiation in accordance with the height of an anatomical organ, the amount of irradiation of a subject can be optimized.

As will be readily understood, the present invention can be achieved by providing an apparatus or system with a storage medium storing program code of software implementing the functions of the apparatus or system according to the embodiment so that a computer (CPU, MPU, or the like) of the apparatus or system is allowed to read and execute the program code stored in the storage medium.

In that case, the functions of the embodiments are achieved by the program code read from the storage medium, so that the program code and the storage medium storing the program code fall within the scope of the present invention.

The storage medium for supplying the program code may be, for example, a ROM, a floppy disk, a hard disk, an optical disk, a magneto-optical disk, a CD-ROM, a CD-R, a magnetic tape, or a non-volatile memory card.

As well as achieving the functions of embodiments by a computer reading and executing the program code, an operating system (OS) or the like running on the computer may execute actual processing in part or in entirety to achieve the functions of the embodiment. This also falls within the scope of the present invention.

Also, the program code read from the storage medium may be written to a memory of a function extension board placed in a computer or a function extension unit connected to the computer so that a CPU or the like of the function extension board or the function extension unit executes actual processing in part or in entirety to achieve the functions of the embodiment. This also falls within the scope of the present invention.

When the present invention is implemented in the form of the program or the storage medium storing the program, the program includes program code corresponding to the flowcharts shown in FIG. 3 and FIG. 6.

As described above, a radiographic apparatus, a radiographic method, a program, and a computer-readable storage medium that allow a position of a subject relative to an X-ray generator and a two-dimensional detector by extracting information regarding a region of an anatomical organ from projection-image data can be provided.

While the present invention has been described with reference to exemplary embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

This application claims priority from Japanese Patent Application No. 2003-417976 filed Dec. 16, 2003, which is hereby incorporated by reference herein.

What is claimed is:

1. A radiographic apparatus comprising:
   an X-ray generator operable to irradiate X-rays at a subject;
   a rotating unit operable to rotate the subject irradiated with the X-rays;
   a two-dimensional detector converting the X-rays transmitting through the subject to obtain projection-image data;
   an information extracting unit extracting information including information regarding the subject from the projection-image data;
   a calculating unit calculating an amount of shift, with respect to a vertical direction, of at least one of the X-ray generator, the two-dimensional detector, and the subject, based on the information extracted by the information extracting unit;
   a driving unit changing a position, with respect to the vertical direction, of at least one of the X-ray generator, the two-dimensional detector, and the subject; and
   a controlling unit controlling the driving unit according to the amount of shift calculated by the calculating unit.

2. The radiographic apparatus according to claim 1, wherein the information extracting unit extracts region information regarding a region of an anatomical organ of the subject from the projection-image data, and wherein the calculating unit calculates the amount of shift based on the region information.

3. The radiographic apparatus according to claim 1, further comprising a reconstructing unit reconstructing the projection-image data obtained by the two-dimensional detector into three-dimensional image data.

4. The radiographic apparatus according to claim 1, wherein the driving unit is coupled to the rotating unit to move the rotating unit so as to change the position of the subject with respect to the vertical direction.

5. The radiographic apparatus according to claim 2, wherein the calculating unit calculates the amount of shift based on at least one of a geometric center position of the region of the anatomical organ and a center of gravity of the region of the anatomical organ.

6. The radiographic apparatus according to claim 2, wherein the anatomical organ includes at least one of a lung region and a chest.

7. The radiographic apparatus according to claim 1, further comprising an X-ray aperture changing unit restricting a range of the X-rays emitted by the X-ray generator based on the information regarding the subject.

8. A radiographic method of radiographing a subject with a radiographic apparatus including an X-ray generator, a rotating unit, and a two-dimensional detector, the radiographic method comprising the following steps:

irradiating the subject with X-rays from the X-ray generator to obtain projection-image data;

extracting information regarding the subject from the projection-image data;

calculating an amount of shift, with respect to a vertical direction, of at least one of the X-ray generator, the two-dimensional detector, and the subject, based on the information extracted in the information extracting step; and changing a position, with respect to the vertical direction, of at least one of the X-ray generator, the two-dimensional detector, and the subject, according to the amount of shift calculated in the calculating step.

9. A program stored on a recording medium and executable by a computer to perform the radiographic method according to claim 8.

10. A computer-readable storage medium having recorded thereon the program according to claim 9.

* * * * *